US012576112B2

(12) United States Patent
O'Heeron et al.

(10) Patent No.: US 12,576,112 B2
(45) Date of Patent: Mar. 17, 2026

(54) INHIBITION OF TNF-ALPHA BY FIBROBLASTS AND FIBROBLAST EXOSOMES

(71) Applicant: SPINALCYTE LLC, Houston, TX (US)

(72) Inventors: Pete O'Heeron, Houston, TX (US); Thomas Ichim, San Diego, CA (US)

(73) Assignee: SPINALCYTE LLC, Houston, TX (US)

( * ) Notice: Subject to any disclaimer, the term of this patent is extended or adjusted under 35 U.S.C. 154(b) by 835 days.

(21) Appl. No.: 17/757,387

(22) PCT Filed: Dec. 22, 2020

(86) PCT No.: PCT/US2020/066602
§ 371 (c)(1),
(2) Date: Jun. 15, 2022

(87) PCT Pub. No.: WO2021/133798
PCT Pub. Date: Jul. 1, 2021

(65) Prior Publication Data
US 2023/0023269 A1     Jan. 26, 2023

Related U.S. Application Data

(60) Provisional application No. 62/953,847, filed on Dec. 26, 2019.

(51) Int. Cl.
*A61K 35/33*        (2015.01)
*A61P 37/00*        (2006.01)
*C12N 15/79*        (2006.01)

(52) U.S. Cl.
CPC .............. *A61K 35/33* (2013.01); *A61P 37/00* (2018.01); *C12N 15/79* (2013.01)

(58) Field of Classification Search
CPC ................ C12N 5/0622; C12N 5/0656; C12N 2502/086
See application file for complete search history.

(56) References Cited

FOREIGN PATENT DOCUMENTS

| | | |
|---|---|---|
| WO | 2009/014633 A1 | 1/2009 |
| WO | 2019/108756 A1 | 6/2019 |
| WO | WO 2019/213518 | 11/2019 |

OTHER PUBLICATIONS

Chen et al., "Adiponectin Inhibits TNF-α-Activated PAI-1 Expression Via the CAMP-PKA-AMPK-NF-κB Axis in Human Umbilical Vein Endothelial Cells," Cellular Physiology and Biochemistry, 42:2342-2352, 2017.
Ichim et al., "Fibroblasts as an Alternative to Mesenchymal Stem Cells with Successful Treatment and Immune Modulation in EAE model of Multiple Sclerosis," bioFxiv, https://doi.org/10.1101/2020.06.04.133249, 18 p. 2020.
Jeon et al., "In vitro and in vivo downregulation of C3 by lipoteichoic acid isolated from Lactobacillus plantarum K8 suppressed cytokine-mediated complement system activation," FEMS Microbiology Letters, 363(14):fnw140, doi: 10.1093/femsle/fnw140, 2016.
Koizumi et al., "Contribution of TNF-alpha to leukocyte adhesion, vascular leakage, and apoptotic cell death in endotoxin-induced uveitis in vivo," Invest. Opthamol. VIs. Sci., 44(5):2184-91, 2003.
Levi et al., "Tissue factor in infection and severe inflammation," Seminars in Thrombosis and Hemostasis, 32 (1):33-39, 2006. (Abstract only).
PCT International Search Report and Written Opinion issued in International Application No. PCT/US2020/066602, 27 pages, dated Mar. 25, 2021.
Vancheri et al., "Human lung fibroblasts inhibit tumor necrosis factor-alpha production by LPS-activated monocytes," American Journal of Respiratory Cell and Molecular Biology, 15(4):460-466, 1996.
Jalili et al., "Fibroblast cell-based therapy prevents induction of alopecia areata in an experimental model," Cell Transplantation, Jun. 2018, 27(6): 994-1004.
Li et al., "Expression of Indoleamine 2,3-Dioxygenase in Dermal Fibroblasts Functions as a Local Immunosuppressive Factor," Journal of Investigative Dermatology, Apr. 2004, 122(4):953-964.
Office Communication issued in European Patent Application No. 20907558.9, dated Feb. 13, 2024.

*Primary Examiner* — Thane Underdahl
(74) *Attorney, Agent, or Firm* — Norton Rose Fulbright LLP

(57) ABSTRACT

Disclosed are means of suppressing production of the inflammatory cytokine TNF-alpha through contact-dependent and contact-independent means by fibroblast populations and products and/or derivatives of fibroblast populations. In one embodiment, fibroblasts are cultured under conditions allowing proliferation of said fibroblasts, wherein said proliferative status of fibroblasts correlates with the ability to directly suppress TNF-alpha production, and/or to release one or more factors capable of suppressing TNF-alpha production. In one embodiment, fibroblasts are used for treatment of inflammatory diseases by their ability to suppress TNF-alpha production. In other embodiments, conditioned media and/or exosomes of said fibroblasts are utilized to treat inflammatory diseases by their ability to suppress TNF-alpha production.

17 Claims, 5 Drawing Sheets

INHIBITION OF TNF-ALPHA BY FIBROBLASTS AND FIBROBLAST EXOSOMES

This application is a national phase application under 35 U.S.C. § 371 that claims priority to International Application No. PCT/US2020/066602, filed Dec. 22, 2020, which claims priority to U.S. Provisional Patent Application Ser. No. 62/953,847, filed Dec. 26, 2019, both of which are incorporated by reference herein in their entirety.

TECHNICAL FIELD

Embodiments of the field of the present disclosure include at least the fields of molecular biology, cell biology, cell therapy, and medicine.

BACKGROUND

TNF alpha is an inflammatory cytokine that was discovered subsequent to administration of *Streptococcus pyogenes* and *Serratia marcescens*, which possessed therapeutic activity and became widely used in the USA prior to the advent of chemotherapy and radiotherapy. In the 1960s, attempts to identify the molecular mechanisms by which *Serratia marcescens* induced tumor regression led to the discovery of a "factor" in the sera of treated mice [1], this factor was identified in 1975 as "Tumor Necrosis Factor" (TNF-alpha) [2]. Interestingly, experiments demonstrated that the same factor that was inducible in sera of mice subsequent to treatment with endotoxin, was also inducible with known immune stimulants *bacillus* Calmette-Guerin (BCG), zymosan, and Corynebacteria. The isolated factor was capable of inducing direct killing of tumor cells in vitro, but not of proliferating, non-malignant murine embryonic cells. Molecular analysis led to cloning of the cDNA, revealed the molecule was comprised of 233 amino acids with a leader sequence of the first 76 amino acids [3, 4]. Interestingly, it was found that the same sequence belonged to another factor associated with cancer: Cachectin [5]. Cachectin was originally demonstrated to mediating weight loss and altering normal metabolic priorities through its effects on both the central nervous system (CNS) and peripheral tissues. Early studies showed that administration of cachectin in animals induces cachexia with a pattern of tissue wasting that includes whole-body protein depletion, unlike the protein-conserving pattern induced by simple caloric restriction [6, 7]. Given the inflammatory nature of TNF-alpha, studies where performed to assess its role in endotoxin-induced shock models.

TNF-alpha is found in a soluble and membrane-bound form. The soluble plasma form of TNF-alpha is cleaved from the membrane forms by a metalloproteinase termed TNF-alpha-converting enzyme (TACE) which belongs to the ADAMs family of disintegrins [8]. Soluble TNF-alpha is 17-kDa protein consisting of 157 amino acids that is a homotrimer in solution. TNF-alpha is mainly produced by activated macrophages, T lymphocytes, and natural killer (NK) cells. A related but distinct cytokine, TNF-beta, previously known as Lymphotoxin, was characterized to share some of the activity of TNF-alpha [9-11]. At present count, there are 19 members of the TNF family and 29 receptors that have been characterized [12].

The activity of TNF is mediated through two cell surface receptors, TNF-R1 (p55) and TNF-R2 (p75) that differ in their signaling activity: TNFR1 is usually pro-apoptotic, whereas TNFR2 is usually anti-apoptotic [13]. TNFR1 and TNFR2 have similar extracellular TNF-binding structures characterized by four repeated cysteine-rich domains but have different intracellular domains [14]. The main structural difference between TNFR1 and TNFR2 that accounts for their divergent biological activity resides in that TNFR2 lacks an intracellular death domain. Thus, in many systems, TNF-alpha promotes apoptosis through activating TNFR1 but causes pro-survival signaling through TNFR2 [15-19]. After binding TNF-alpha, TNFR1 recruits the adaptor protein TNFR1-associated death domain protein (TRADD) and its downstream caspases causing apoptosis [12, 20, 21]. Conversely, when TNF-alpha activates TNFR2, recruitment of the TNF receptor-associated factor (TRAF) 2 occurs, resulting in stimulation of NF-kappa B, which possesses anti-apoptotic properties [22]. The TNFR2 is known to possess a higher affinity towards membrane bound TNF-alpha as compared to soluble TNF-alpha [23].

While TNFR1 is expressed on various tumor cells [24] and tumor endothelial cells [25], TNFR2 is expressed on various immune cells including T regulatory cells [26, 27], myeloid suppressor cells [28], and some cancer cells [29, 30]. Various complex interplays between receptors have been described based on in vitro studies, which in some cases are contradictory.

Although a variety of antibodies exist that bind TNF-alpha, these possess numerous toxicities, as well as off target lack of specificity. The present disclosure concerns the use of fibroblasts and their products to inhibit TNF-alpha production.

BRIEF SUMMARY

Embodiments of the disclosure provide methods and compositions related to the use of fibroblasts and/or their products to suppress or inhibit TNF-alpha production. In particular embodiments, the methods and compositions provide treatment or prevention of one or more medical conditions associated with TNF-alpha, including excess TNF-alpha over normal levels. In specific embodiments, the methods and compositions provide treatment or prevention of inflammation directly and/or indirectly related to the production of TNF-alpha.

In specific embodiments, a method of suppressing production of TNF-alpha from a cell includes contacting a cell capable of producing TNF-alpha with fibroblasts and/or one or more products generated by said fibroblasts. In specific embodiments, said cell capable of making TNF-alpha is a mammalian cell. In specific embodiments, said mammalian cell is an immune cell and selected from a group consisting of: a) monocytes; b) macrophages; c) Th17 cells; d) endothelial cells; d) parenchymal cells, e) microglial cells, f) astrocyte cells, and g) a combination thereof. In specific embodiments, said fibroblast is in a proliferative state. In specific embodiments, said fibroblast is derived from a tissue selected from a group of tissues consisting of: a) placenta; b) skin; c) adipose tissue; e) bone marrow; f) omentum; g) hair follicle; h) peripheral blood; i) mobilized peripheral blood; j) endometrium; k) synovial fluid; l) foreskin; and m) a combination thereof.

In specific embodiments, said fibroblasts are activated with one or more agents that resemble inflammation prior to being used to suppress TNF-alpha. Such agents that induce inflammation may be selected from a group comprising of: interleukin-1, interleukin-6, interleukin-8, TNF-alpha, Interferon alpha, and Interferon gamma. In specific embodiments, suppression of TNF-alpha is utilized to inhibit one or more inflammatory diseases. In specific embodiments, said inflammatory disease is an autoimmune disease. In specific embodiments, said autoimmune disease is selected from a group of diseases consisting of: rheumatoid arthritis (RA), Insulin dependent Diabetes (Type I), Alopecia Areata, Ankylosing Spondylitis, Antiphospholipid Syndrome, Autoimmune Addison's Disease, Autoimmune Hemolytic Anemia, Autoimmune Hepatitis, Behcet's Disease, Bullous Pemphigoid, Cardiomyopathy, Celiac Sprue-Dermatitis, Chronic Fatigue Immune Dysfunction Syndrome (CFIDS), Chronic Inflammatory Demyelinating Polyneuropathy, Churg-Strauss Syndrome Cicatricial Pemphigoid, CREST Syndrome, Cold Agglutinin Disease, Crohn's Disease, Discoid Lupus, Essential Mixed Cryoglobulinemia, Fibromyalgia-Fibromyositis, Guillain-Barre, Hashimoto's Thyroiditis, Idiopathic Pulmonary Fibrosis, Idiopathic Thrombocytopenia Purpura (ITP), IgA Nephropathy, Juvenile Arthritis, Lichen Planus, Lupus, Meniere's Disease, Mixed Connective Tissue Disease, Multiple Sclerosis, Myasthenia Gravis, Pemphigus Vulgaris, Pernicious Anemia, Polyarteritis Nodosa, Polychondritis, Polyglandular Syndromes, Polymyalgia Rheumatica, Polymyositis and Dermatomyositis, Primary Agammaglobulinemia, Primary Biliary Cirrhosis, Psoriasis, Raynaud's Phenomenon, Reiter's Syndrome, Rheumatic Fever, Sarcoidosis, Scleroderma, Sjogren's Syndrome, Stiff-Man Syndrome, Takayasu Arteritis, Temporal Arteritis/Giant Cell Arteritis, Ulcerative Colitis, Uveitis, Vasculitis, Vitiligo, Wegener's Granulomatosis, and a combination thereof.

In specific embodiments, suppression of TNF-alpha includes suppression of the effects of TNF-alpha on cells. In specific embodiments, said suppression of effects of TNF-alpha includes suppression of vascular leakage; suppression of NF-kappa B activation; suppression of tissue factor expression; suppression of upregulation of one or more complement activators; or a combination thereof.

In specific embodiments, said product generated by said fibroblast comprises an exosome or a plurality of exosomes. In specific embodiments, said exosomes express phosphatidylserine on their membrane. In specific embodiments, said exosomes are between 80-200 nanometers in diameter. In specific embodiments, apoptotic bodies from fibroblasts are utilized as a replacement for fibroblasts or in addition to fibroblasts or other fibroblast products to inhibit TNF-alpha production. Conditioned media from fibroblasts may alternatively or additionally be used with fibroblasts or other fibroblast products.

Embodiments of the disclosure include methods of treating an individual for an inflammatory disease, comprising the step of administering to an individual in need thereof a therapeutically effective amount of fibroblasts and/or a product generated by or derived from said fibroblasts. The individual in need thereof may have the inflammatory disease or is at risk for having the inflammatory disease, including any an autoimmune disease. Examples of autoimmune diseases includes rheumatoid arthritis (RA), Insulin dependent Diabetes (Type I), Alopecia Areata, Ankylosing Spondylitis, Antiphospholipid Syndrome, Autoimmune Addison's Disease, Autoimmune Hemolytic Anemia, Autoimmune Hepatitis, Behcet's Disease, Bullous Pemphigoid, Cardiomyopathy, Celiac Sprue-Dermatitis, Chronic Fatigue Immune Dysfunction Syndrome (CMS), Chronic Inflammatory Demyelinating Polyneuropathy, Churg-Strauss Syndrome Cicatricial Pemphigoid, CREST Syndrome, Cold Agglutinin Disease, Crohn's Disease, Discoid Lupus, Essential Mixed Cryoglobulinemia, Fibromyalgia-Fibromyositis, Guillain-Barre, Hashimoto's Thyroiditis, Idiopathic Pulmonary Fibrosis, Idiopathic Thrombocytopenia Purpura (ITP),

4

IgA Nephropathy, Juvenile Arthritis, Lichen Planus, Lupus, Meniere's Disease, Mixed Connective Tissue Disease, Multiple Sclerosis, Myasthenia Gravis, Pemphigus Vulgaris, Pernicious Anemia, Polyarteritis Nodosa, Polychondritis, Polyglandular Syndromes, Polymyalgia Rheumatica, Polymyositis and Dermatomyositis, Primary Agammaglobulinemia, Primary Biliary Cirrhosis, Psoriasis, Raynaud's Phenomenon, Reiter's Syndrome, Rheumatic Fever, Sarcoidosis, Scleroderma, Sjogren's Syndrome, Stiff-Man Syndrome, Takayasu Arteritis, Temporal Arteritis/Giant Cell Arteritis, Ulcerative Colitis, Uveitis, Vasculitis, Vitiligo, or Wegener's Granulomatosis. In any method encompassed herein, suppression of TNF-alpha comprises suppression of the effects of TNF-alpha on cells in the individual, such as suppression of vascular leakage in the individual, suppression of NF-kappa B activation in the individual, suppression of tissue factor expression in the individual, suppression of upregulation of complement activators in the individual. In any method encompassed herein, fibroblasts are derived from a tissue selected from the group of tissues consisting of: a) placenta; b) skin; c) adipose tissue; e) bone marrow; f) omentum; g) hair follicle; h) peripheral blood; i) mobilized peripheral blood; j) endometrium; k) synovial fluid; l) foreskin; and m) a combination thereof. Also, in any method, the fibroblasts are in a proliferative state and/or are capable of differentiating into mesoderm, ectoderm, and/or endoderm. In any method encompassed herein, fibroblasts are regenerative fibroblasts. Any fibroblasts may express one or more of Oct-4, Nanog, Sox-2, KLF4, c-Myc, Rex-1, GDF-3, LIF receptor, CD105, CD117, CD344, Stella, CD10, CD13, CD44, CD73, CD90, CD141, PDGFr-alpha, HLA-A, HLA-B, HLA-C, FoxD3, and Polycomb embryonic transcription factors. Any fibroblasts may not express one or more of MHC class I, MHC class II, CD44, CD45, CD13, CD49c, CD66b, CD73, CD90, CD31, CD34, CD141, and HLA-DR, DP,DQ.

In any method encompassed herein, cells selected from the group consisting of granulocytes, T-cells, B-cells, NK-cell, red blood cells, cells expressing stem cell surface markers, cells expressing MHC proteins, or any combination thereof, are separated from fibroblasts prior to any contacting step, and they may be separated from the fibroblasts by cell depletion. In any methods encompassed herein, fibroblasts are transfected with a polynucleotide vector, such as one containing a promoter operably linked to a reporter or selection gene, and this may occur prior to any contacting step. The promoter may be a fibroblast cell-specific promoter and/or a regenerative tissue cell-specific promoter. The promoter may be a fibroblast cell-specific promotor and/or may be selected from the group consisting of Oct-4, Nanog, Sox-9, GDF3, Rex-1, Sox-2 Stella, FoxD3, Polycomb Repressor Complex 2, and aCTCF promoters. In some aspects, the fibroblast cell-specific promoter is flanked by loxP sites. Any promoter may be constitutive or inducible.

In any method encompassed herein, a population of fibroblasts is enriched, such as using expression of said reporter or selection gene prior to said contacting step and/or by flow cytometry prior to any contacting step. In specific embodiments, the population of said fibroblasts in a proliferative state are enriched prior to said contacting step, the enriching step further comprising the steps of: contacting said fibroblasts with a detectable compound that enters the fibroblasts, wherein the compound is selectively detectable in proliferating and non-proliferating fibroblasts; and enriching the population of fibroblasts for proliferating fibroblasts. A detectable compound may be carboxyfluorescein diacetate, succinimidyl ester, or Aldefluor. In any method encompassed herein, fibroblasts are transfected with a Oct-4, Nanog, Sox-2, and/or KLF prior to said contacting step. The fibroblasts may further comprise enhanced regenerative activity compared to a control. In any method encompassed herein, the fibroblasts are fused with cells having a pluripotent ability prior to said contacting step. In some embodiments, fibroblasts further comprise enhanced regenerative activity compared to a control. In specific aspects, fibroblast cells expressing CD105 and/or CD 117 are transfected with NANOG gene. The fibroblasts may further comprise rhodamine 123 efflux activity as compared to a control. The fibroblasts may further comprise enhanced expression of GDF-11 as compared to a control. The fibroblasts may be cultured under conditions that form tissue aggregate bodies prior to said contacting step and/or are cultured under conditions that support fibroblast proliferation prior to said contacting step and/or are activated with one or more agents that resembles inflammation prior to said contacting step.

The foregoing has outlined rather broadly the features and technical advantages of the present disclosure in order that the detailed description that follows may be better understood. Additional features and advantages will be described hereinafter which form the subject of the claims herein. It should be appreciated by those skilled in the art that the conception and specific embodiments disclosed may be readily utilized as a basis for modifying or designing other structures for carrying out the same purposes of the present designs. It should also be realized by those skilled in the art that such equivalent constructions do not depart from the spirit and scope as set forth in the appended claims. The novel features which are believed to be characteristic of the designs disclosed herein, both as to the organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

BRIEF DESCRIPTION OF THE DRAWINGS

For a more complete understanding of the present disclosure, reference is now made to the following descriptions taken in conjunction with the accompanying drawing, in which.

DETAILED DESCRIPTION

I. Examples of Definitions

Figure 1:
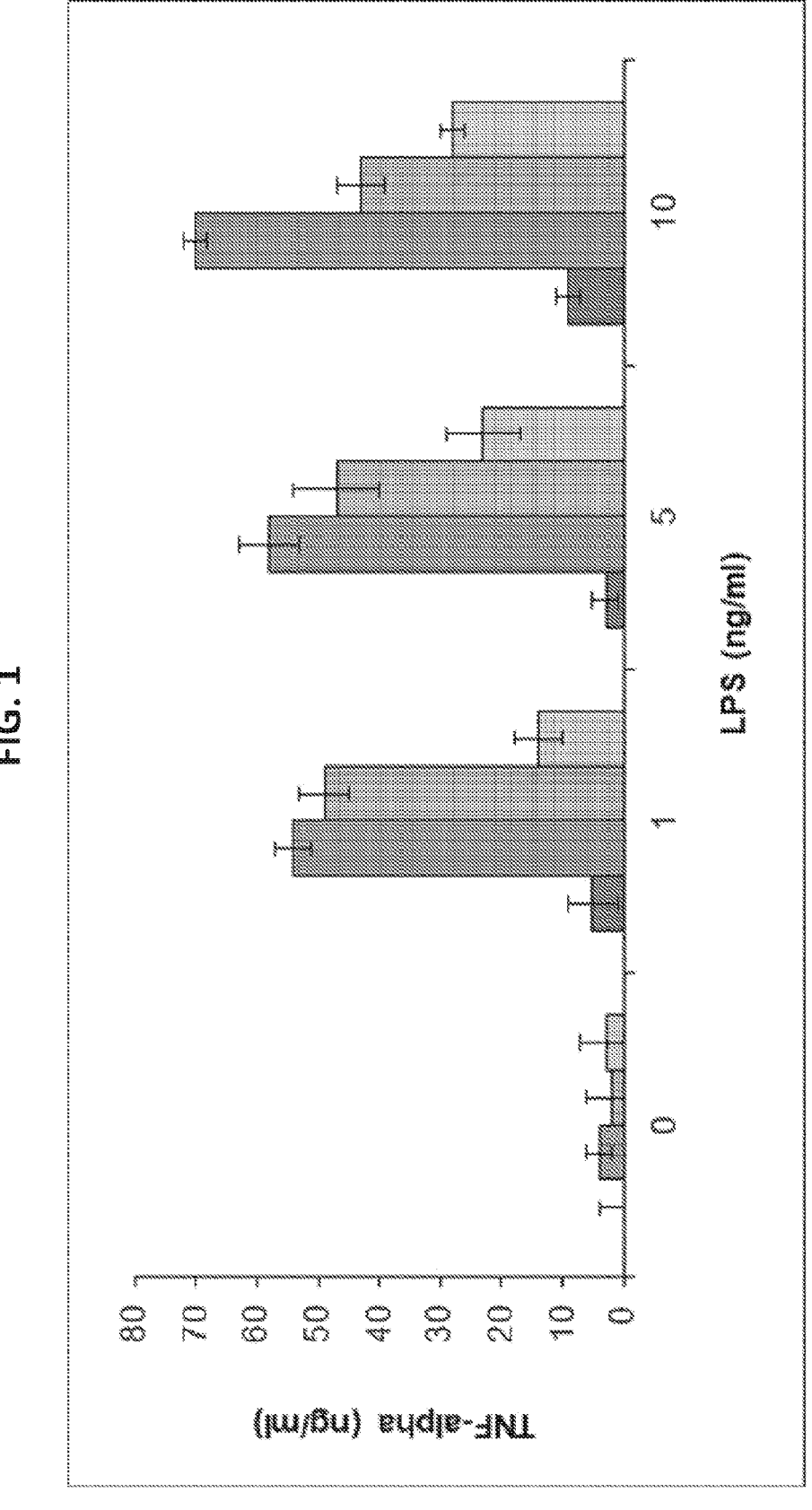
FIG. 1 shows in vitro suppression of TNF-alpha production by LPS activated monocytes using treatment with proliferating fibroblasts compared to treatment with mitotically inactivated fibroblasts, culture controls, and LPS alone. The order of bars on the figure from left to right are culture controls, LPS alone, mitotically inactivated fibroblasts, and proliferating fibroblasts.

In keeping with long-standing patent law convention, the words "a" and "an" when used in the present specification in concert with the word comprising, including the claims, denote "one or more." Some embodiments of the disclosure may consist of or consist essentially of one or more elements, method steps, and/or methods of the disclosure. It is contemplated that any method or composition described herein can be implemented with respect to any other method or composition described herein and that different embodiments may be combined.

As used herein, the terms "or" and "and/or" are utilized to describe multiple components in combination or exclusive of one another. For example, "x, y, and/or z" can refer to "x" alone, "y" alone, "z" alone, "x, y, and z," "(x and y) or z," "x or (y and z)," or "x or y or z." It is specifically contemplated that x, y, or z may be specifically excluded from an embodiment.

Throughout this application, the term "about" is used according to its plain and ordinary meaning in the area of cell and molecular biology to indicate that a value includes the standard deviation of error for the device or method being employed to determine the value.

The term "comprising," which is synonymous with "including," "containing," or "characterized by," is inclusive or open-ended and does not exclude additional, unrecited elements or method steps. The phrase "consisting of" excludes any element, step, or ingredient not specified. The phrase "consisting essentially of" limits the scope of described subject matter to the specified materials or steps and those that do not materially affect its basic and novel characteristics. It is contemplated that embodiments described in the context of the term "comprising" may also be implemented in the context of the term "consisting of" or "consisting essentially of."

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments.

A variety of aspects of this disclosure can be presented in a range format. It should be understood that the description in range format is merely for convenience and brevity and should not be construed as an inflexible limitation on the scope of the present disclosure. Accordingly, the description of a range should be considered to have specifically disclosed all the possible subranges as well as individual numerical values within that range as if explicitly written out. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. When ranges are present, the ranges may include the range endpoints.

"Express" and "expression" refer to the process by which information (e.g., genetic and/or epigenetic information) is converted into the structures present in a cell or secreted therefrom. Accordingly, as used herein, "expression" may refer to transcription, translation, or polynucleotide and/or polypeptide modifications (e.g., posttranslational modification of a polypeptide).

"Genetically modified fibroblast" is a fibroblast cell that recombinantly expresses a modification to gene expression compared to its native state, including by the hand of man. Gene modification can be at least (1) enhanced expression of one or more genes endogenous to the cell (such as by modifying one or more regulatory sequences for the gene); (2) suppressed expression of one or more genes endogenous to the cell (such as through RNA interference or gene editing, for example with CRISPR); and/or (3) expression of one or more recombinant genes (whether or not the gene is also present as a genomic, endogenous copy in the cell), such as from a transfected vector that may or may not be integrating into the fibroblast genome.

"Pharmaceutical composition" as used herein refers to any composition that comprises one or more therapeutically or biologically active agents such as cells, exosomes, apoptotic bodies, and/or conditioned media thereof.

The term "subject," as used herein, may be used interchangeably with the term "individual" and generally refers to an individual in need of a therapy. The subject can be a mammal, such as a human, dog, cat, horse, pig or rodent. The subject can be a patient, e.g., have or be suspected of having or at risk for having a disease or medical condition, including for inflammation, for example. For subjects having or suspected of having a medical condition directly or indirectly associated with inflammation, the medical condition may be of one or more types. The subject may have a disease or be suspected of having the disease. The subject may be asymptomatic. The subject may be of any gender. The subject may be of a certain age, such as at least 30, 35, 40, 45, 50, 55, 60, 65, 70, 75, 80, 85, 90, 95, or 100 or more.

"Treatment," "treat," or "treating" means a method of reducing the effects of a disease or condition. Treatment can also refer to a method of reducing the disease or condition itself rather than just the symptoms. The treatment can be any reduction from pre-treatment levels and can be but is not limited to the complete ablation of the disease, condition, or the symptoms of the disease or condition. Therefore, in the disclosed methods, treatment" can refer to a 10%, 20%, 30%, 40%, 50%, 60%, 70%, 80%, 90%, or 100% reduction in the severity of an established disease or the disease progression, including reduction in the severity of at least one symptom of the disease. For example, a disclosed method for reducing the immunogenicity of cells is considered to be a treatment if there is a detectable reduction in the immunogenicity of cells when compared to pre-treatment levels in the same subject or control subjects. Thus, the reduction can be a 10, 20, 30, 40, 50, 60, 70, 80, 90, 100%, or any amount of reduction in between as compared to native or control levels. It is understood and herein contemplated that "treatment" does not necessarily refer to a cure of the disease or condition, but an improvement in the outlook of a disease or condition. In specific embodiments, treatment refers to the lessening in severity or extent of at least one symptom and may alternatively or in addition refer to a delay in the onset of at least one symptom.

The term "extracellular vesicle" as used herein is a particle naturally released from virtually every cell type in the body that is surrounded by a phospholipid bilayer and cannot replicate. Extracellular vesicles contain distinct lipids, proteins, sugars, adhesion integrins, growth factors, receptors, cytokines, protease inhibitors, and nucleic acids that reflect their cells of origin. Extracellular vesicles include exosomes (generally ranging from 30-150 nm), microvesicles (generally ranging from 30 nm-2 μm), and apoptotic bodies (500 nm-2 μm).

The term "conditioned media" as used herein is the spent media harvested from cultured cells. It contains metabolites, growth factors, and extracellular matrix proteins secreted into the medium by the cultured cells. Examples may include metabolites such as glucose, amino acids, and nucleosides; growth factors such as interleukins, EGF (epidermal growth factor), and PDGF (platelet-derived growth factor); and matrix proteins such as collagen, fibronectin, and various proteoglycans. Fibroblasts are extremely heterogeneous multi-functional cells that play a role in wound healing, developmental processes, and tumor development. Fibroblasts are capable of producing and releasing into the culture media various immune modulators including peptide growth factors, cytokines, chemokines and inflammatory mediators.

This disclosure is not limited to the particular methodology, protocols, and reagents, etc., described herein and as such can vary. The terminology used herein is for the purpose of describing particular embodiments only, and is not intended to limit the scope of the present invention, which is defined solely by the claims. As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about." All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents. Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

II. Uses of Fibroblasts and Derivatives Thereof

The present disclosure encompasses that fibroblasts, and/or derivatives of fibroblasts, are capable of suppressing production of TNF-alpha. In particular, the disclosure provides methods and compositions concerning proliferating fibroblasts that possess the ability to increase suppression of TNF-alpha production as compared to control non-proliferating fibroblasts. The disclosure also encompasses use of proliferating fibroblasts to treat medical conditions for which they are therapeutic, and providing them to an individual in need. thereof.

III. Fibroblasts, Fibroblast Derivatives, and Manipulation and/or Production Thereof In some embodiments the disclosure encompasses the use of isolated fibroblast cells or a population thereof, and/or fibroblast derivatives (e.g., apoptotic bodies) and/or products of fibroblasts (exosomes) capable of proliferating and differentiating into ectoderm, mesoderm, or endoderm, wherein the isolated fibroblast cell(s) expresses at least one of Oct-4, Nanog, Sox-2, KLF4, c-Myc, Rex-1, GDF-3, LIF receptor, CD105, CD117, CD344 or Stella markers, and does not express at least one of MHC class I, MHC class II, CD45, CD13, CD49c, CD66b, CD73, CD105, or CD90 cell surface proteins. Use of derivatives of such fibroblasts is also encompassed herein. These cells are used as a source of conditioned media, in some embodiments, and the cells may be cultured alone, or may by cultured in the presence of other cells, such as in order to further upregulate production of one or more growth factors in the conditioned media.

The fibroblasts may be expanded and utilized for administration themselves, or they may be cultured in a growth media in order to obtain conditioned media, and in specific aspects the term growth medium or growth media generally refers to a medium sufficient for the culturing of fibroblasts. In particular, one particular medium for the culturing of the cells of the disclosure herein comprises Dulbecco's Modified Essential Media (also abbreviated DMEM herein). In specific aspects, the media is DMEM-low glucose (also DMEM-LG herein) (Invitrogen, Carlsbad, Calif.). The DMEM-low glucose may be supplemented with 15% (v/v) fetal bovine serum (e.g. defined fetal bovine serum, Hyclone, Logan Utah), antibiotics/antimycotics (preferably penicillin (100 Units/milliliter), streptomycin (100 milligrams/milliliter), and amphotericin B (0.25 micrograms/milliliter), (Invitrogen, Carlsbad, Calif.)), and 0.001% (v/v) 2-mercaptoethanol (Sigma, St. Louis Mo.). In some cases different growth media are used, or different supplementations are provided, and these are normally indicated in the text as supplementations to growth medium. Also relating to the present disclosure, the term standard growth conditions, as used herein refers to culturing of cells at 37° C., in a standard atmosphere comprising 5% $CO_2$. Relative humidity is maintained at about 100%. While foregoing the conditions are useful for culturing, it is to be understood that such conditions are capable of being varied by the skilled artisan who will appreciate the options available in the art for culturing cells, for example, varying the temperature, $CO_2$, relative humidity, oxygen, growth medium, and the like. In cases wherein fibroblast products or derivatives are utilized, the fibroblasts may or may not be expanded prior to obtaining or use of the products or derivatives.

Methods are provided wherein fibroblast cells that are used in the disclosure can undergo at least 25, 30, 35, or 40 doublings prior to reaching a senescent state. Methods for deriving cells capable of doubling to reach $10^{14}$ cells or more are provided. In some cases, those methods that derive cells that can double sufficiently to produce at least about $10^{14}$, $10^{15}$, $10^{16}$, or $10^{17}$ or more cells when seeded at from about $10^3$ to about $10^6$ cells/cm$^2$ in culture. Preferably these cell numbers are produced within 80, 70, or 60 days or less. In one embodiment, fibroblast cells used for the generation of conditioned media are isolated and expanded, and possess one or more markers selected from the group consisting of CD10, CD13, CD44, CD73, CD90, CD141, PDGFr-alpha, HLA-A,B,C, and a combination thereof. In addition, the cells do not produce one or more of CD31, CD34, CD45, CD117, CD141, or HLA-DR,DP,DQ.

In some embodiments, the methods utilize regenerative fibroblasts (fibroblasts that are regenerative themselves and/or that can also endow other tissues/cells to possess regenerative activity). For isolating a population of regenerative fibroblast cells, the method comprises providing a tissue with regenerative activity (e.g., placenta, bone marrow, endometrium, etc.); and enriching for a population of cells that are about 6-12 micrometers in size, wherein the fibroblast regenerative cells express at least one of Oct-4, Nanog, Sox-2, KLF4, c-Myc, Rex-1, GDF-3, LIF receptor, CD105, CD117, CD344 and Stella, and does not express at least one of MHC class I, MHC class II, CD45, CD13, CD49c, CD66b, CD73, or CD90 cell surface proteins. In some embodiments, the cells lack expression of CD105 and/or CD117, and in other embodiments, the cells express CD105 and/or CD117.

In some aspects, the method optionally includes transfecting the cells with a polynucleotide vector containing a suitable promoter (such as a fibroblast cell-specific promoter) operably linked to a reporter or selection gene. In some aspects, the promoter is an Oct-4, Nanog, Sox-9, GDF3, Rex-1, or Sox-2 promoter. In certain cases, the promoter is constitutive or inducible or tissue-specific. In some embodiments, the method further includes the step of enriching the population for the regenerative fibroblast cells using expression of a reporter or selection gene. In some embodiments, the method further includes the step of enriching the population of the regenerative fibroblast cells by flow cytometry. In some embodiments, the method further includes the steps of contacting the cells with a detectable compound that enters the cells, the compound being selectively detectable in proliferating and non-proliferating cells; and enriching the population of cells for the proliferating cells. In some aspects, the detectable compound is carboxyfluorescein diacetate, succinimidyl ester, or Aldefluor. In some embodiments, any of the methods further include culturing the cells under conditions that form tissue aggregate bodies. In some embodiments, the method further includes culturing the population of fibroblast regenerative cells under conditions that support proliferation of the cells.

In some embodiments, the method further includes separating cell types such as granulocytes, T-cells, B-cells, NK-cell, red blood cells, or any combination thereof, from the fibroblast regenerative cells. In some aspects, separating the cell types is done by cell depletion. Further embodiments of the current disclosure relate to a method of identifying a fibroblast regenerative cell, the method comprises the steps of introducing into a cell a vector comprising a fibroblast cell-specific promoter coupled to at least one selectable marker gene; expressing the selectable marker gene from the cell specific promoter in the cell; and detecting expression of the marker gene or gene product in the cell, thereby identifying the fibroblast regenerative cell, wherein said fibroblast regenerative cell does not express at least one or more of MHC class I, MHC class II, CD44, CD45, CD13, CD34, CD49c, CD66b, CD73, CD105, and CD90 cell surface proteins; and said fibroblast regenerative cell expresses at least one or more of Oct-4, Nanog, Sox-2, Rex-1, GDF-3, Stella, FoxD3, or Polycomb embryonic transcription factors, and wherein said fibroblast regenerative cell is capable of differentiating into mesoderm, ectoderm, and/or endoderm. In some embodiments, the fibroblast cell does not express CD13, CD44, CD90, or a combination thereof.

In some embodiments, the fibroblast cell-specific promoter is an Oct-4 promoter, a Nanog promoter, a Sox-2 promoter, a Rex-1 promoter, a GDF-3 promoter, a Stella promoter, a FoxD3 promoter, a Polycomb Repressor Complex 2 promoter, or aCTCF promoter. In some embodiments, the fibroblast cell-specific promoter is flanked by loxP sites.

In some embodiments, the method further comprises the step of isolating the fibroblast regenerative cell(s). In some aspects the fibroblast regenerative cell is derived from one or more bodily fluids and/or from one or more tissues of a mammal. In some embodiments, the bodily fluid is synovial fluid and/or blood. In some embodiments, the mammal is a human. Examples of tissue sources include at least the following: a) placenta; b) skin; c) adipose tissue; e) bone marrow; f) omentum; g) hair follicle; h) peripheral blood; i) mobilized peripheral blood; j) endometrium; k) synovial fluid; l) foreskin; and m) a combination thereof.

In some embodiments, the vector is a viral vector or non-viral vector. Examples of viral vectors include retroviral vectors, lentiviral vectors, adenoviral vectors, or adeno-associated viral vectors. In some embodiments, the selectable marker gene encodes a fluorescent protein, such as but limited to Green Fluorescent Protein (GFP). In some embodiments, the vector comprises two selectable marker genes, the two selectable marker genes comprise a fluorescent protein, a protein sensitive to drug selection, a cell surface protein or any combination thereof. Further aspects of the disclosure relate to a method of generating a regenerative fibroblast cell comprising the steps of introducing into a population of fibroblasts a vector comprising a promoter, such as a regenerative cell-specific promoter (promoters associated with regeneration, such as promoters for NANOG or Sox-2), coupled to at least one selectable marker gene, wherein said regenerative cell does not express MHC class I, MHC class II, CD44, CD45, CD13, CD34, CD49c, CD73, CD105 and CD90 cell surface proteins; expressing the selectable marker gene from the regenerative-cell specific promoter in said fibroblast population; and detecting expression of the marker gene in the regenerative fibroblast cell. In some embodiments, the methods further comprise a step of transfecting the regenerative fibroblast cells with a transcription factor that enhances the regenerative activity of the fibroblast cells, such as OCT-4, NANOG, and/or SOX-2 transcription factor. In some embodiments, the methods further comprise a step of fusing the fibroblast cells, including regenerative fibroblast cells, with pluripotent cells, thereby generating fibroblasts with enhanced regenerative activity.

In some embodiments, the methods further comprise the steps of selecting fibroblast cells expressing CD105 and/or CD 117; and transfecting the fibroblast cells expressing CD105 and/or CD 117 with the NANOG and/or SOX-2 and/or OCT-4 gene. In some aspects, the fibroblast regenerative cell further comprises a rhodamine 123 efflux activity. In further aspects, the fibroblast regenerative cell has enhanced expression of GDF-11, such as compared to a control.

Culture conditioned media may be concentrated by filtering/desalting means known in the art, in some aspects. In one embodiment, Amicon filters, or substantially equivalent means, with specific molecular weight cut-offs are utilized, said cut-offs may select for molecular weights higher than 1 kDa to 50 kDa.

The cell culture supernatant may alternatively be concentrated using means known in the art such as solid phase extraction using C18 cartridges (Mini-Spe-ed C18-14%, S.P.E. Limited, Concord ON). The cartridges are prepared by washing with methanol followed by deionized-distilled water. Up to 100 ml of stem cell or progenitor cell supernatant may be passed through each of these specific cartridges before elution, it is understood of one of skill in the art that larger cartridges may be used. After washing the cartridges material adsorbed is eluted with 3 ml methanol, evaporated under a stream of nitrogen, redissolved in a small volume of methanol, and stored at 4° C.

Before testing the eluate for activity in vitro, the methanol is evaporated under nitrogen and replaced by culture medium. The C18 cartridges are used to adsorb small hydrophobic molecules from the stem or progenitor cell culture supernatant, and allows for the elimination of salts and other polar contaminants. It may, however be desired to use other adsorption means in order to purify certain compounds from said fibroblast cell supernatant. Said fibroblast concentrated supernatant may be assessed directly for biological activities useful for the practice of this methods of the disclosure, or may be further purified. In one embodiment, the supernatant of fibroblast culture is assessed for ability to stimulate proteoglycan synthesis using an in vitro bioassay. The in vitro bioassay allows for quantification and knowledge of which molecular weight fraction of supernatant possesses biological activity. Bioassays for testing ability to stimulate proteoglycan synthesis are known in the art. Production of various proteoglycans can be assessed by analysis of protein content using techniques including mass spectrometry, column chromatography, immune based assays such as enzyme linked immunosorbent assay (ELISA), immunohistochemistry, and flow cytometry.

Further purification may be performed using, for example, gel filtration using a Bio-Gel P-2 column with a nominal exclusion limit of 1800 Da (Bio-Rad, Richmond Calif.). Said column may be washed and pre-swelled in 20 mM Tris-HCl buffer, pH 7.2 (Sigma) and degassed by gentle swirling under vacuum. Bio-Gel P-2 material be packed into a 1.5.times.54 cm glass column and equilibrated with 3 column volumes of the same buffer. Amniotic fluid stem cell supernatant concentrates extracted by C18 cartridge may be dissolved in 0.5 ml of 20 mM Tris buffer, pH 7.2 and run through the column. Fractions may be collected from the column and analyzed for biological activity. Other purification, fractionation, and identification means are known to one skilled in the art and include anionic exchange chromatography, gas chromatography, high performance liquid chromatography, nuclear magnetic resonance, and mass spectrometry. Administration of supernatant active fractions may be performed locally or systemically.

IV. Gene Editing Techniques of the Disclosure

The introduction of nucleic acids into cells can be accomplished by various means. In one embodiments, transduction is the infection of a target cell such as the fibroblast by a virus that promotes genetic modification of the target cell. Many viruses bind and infect mammalian cells and can be used to introduce genetic material (e.g., a donor gene, such as a gene encoding a transcription factor or any other gene product) into the host cell as part of their replication cycle. In viruses modified for gene transfer, the donor gene (e.g., a gene encoding a transcription factor or any other gene product) is inserted into the viral genome. Additional modifications may be made to the virus to improve infectivity or tropism (e.g., pseudotyping), to reduce or eliminate replicative competency, and/or to reduce immunogenicity. The newly-introduced donor gene will be expressed in the infected host cell or organism and, if replacing a defective host gene, can ameliorate conditions or diseases caused by the defective gene.

Numerous examples of viral vectors that can be used to deliver genetic material (e.g., a donor gene, such as a gene encoding a transcription factor or any other gene product) include, but are not limited to, a retrovirus, adenovirus (e.g., Ad2, Ad5, Ad11, Ad12, Ad24, Ad26, Ad34, Ad35, Ad40, Ad48, Ad49, Ad50, and Pan9 (also known as AdC68)), parvovirus (e.g., adeno-associated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses, such as picornavirus and alphavirus, and double stranded DNA viruses including adenovirus, herpesvirus (e.g., Herpes Simplex virus types 1 and 2, Epstein-Barr virus, cytomegalovirus), and poxvirus (e.g., vaccinia, modified vaccinia Ankara (MVA), fowlpox and canarypox). Other viruses useful for delivering polynucleotides encoding a transcription factor or any other gene product to a HUCPVC include Norwalk virus, togavirus, flavivirus, reoviruses, papovavirus, hepadnavirus, and hepatitis virus. Adenoviruses and retroviruses (including lentiviruses) are particularly attractive modalities for gene therapy applications, as discussed below, due to the ability to genetically modify and exploit the life cycle of these viruses.

Another means of viral introduction is the utilization of recombinant adenoviral vectors, which offer several significant advantages for the expression of a transcription factor or any other gene product (s) in HUCPVCs. The viruses can be prepared at extremely high titer, infect non-replicating cells, and confer high-efficiency and high-level transduction of target cells in vivo after directed injection or perfusion. Furthermore, as adenoviruses do not integrate their DNA into the host genome, this gene therapy modality has a reduced risk of inducing spontaneous proliferative disorders. In animal models, adenoviral gene transfer has generally been found to mediate high-level expression for approximately one week. The duration of transgene expression may be prolonged, and ectopic expression reduced, by using tissue-specific promoters. Other improvements in the molecular engineering of the adenoviral vector itself have produced more sustained transgene expression and less inflammation. This is seen with so-called "second generation" vectors harboring specific mutations in additional early adenoviral genes and "gutless" vectors in which virtually all the viral genes are deleted utilizing a cre-lox. Examples of adenoviruses that can be used as a viral vector of the invention include those having, or derived from, the serotypes Ad2, Ad5, Ad11, Ad12, Ad24, Ad26, Ad34, Ad35, Ad40, Ad48, Ad49, Ad50, and Pan9 (also known as AdC68).

Recombinant adeno-associated viruses (rAAV), which are derived from non-pathogenic parvoviruses, can be used to express a donor gene, such as a gene encoding a transcription factor or any other gene product (s), as these vectors evoke almost no cellular immune response, and produce transgene expression lasting months in most systems. The AAV genome is built of single stranded DNA, and includes inverted terminal repeats (ITRs) at both ends of the DNA strand, and two open reading frames: rep and cap, encoding replication and capsid proteins, respectively. A donor gene (e.g., a gene encoding a transcription factor or any other gene product) can replace the native rep and cap genes. AAVs can be made with a variety of different serotype capsids which have varying tropism for different tissue types. Examples of AAV serotypes that can be used include but are not limited to AAV1, AAV2, AAV3, AAV4, AAV5, AAV6, AAV7, AAV8, AV9, and AAVrh10. AAV vectors can be produced, for example, by triple transfection of subconfluent HEK293 cells by three plasmids: AAV cis-plasmid containing the donor gene of interest (e.g., a gene encoding a transcription factor or any other gene product), AAV trans-plasmid containing AAV rep and cap genes, and an adenovirus helper plasmid, e.g., pDF6. Incorporation of a tissue-specific promoter is, again, typically beneficial.

Another viral vector that can be used to deliver a gene into a subject or cells is a retrovirus, including a lentivirus. As opposed to adenoviruses, the genetic material in retroviruses is in the form of RNA molecules, while the genetic material of their hosts is in the form of DNA. When a retrovirus infects a host cell, it will introduce its RNA together with some enzymes into the cell. This RNA molecule from the retrovirus will produce a double-stranded DNA copy (provirus) from its RNA molecules through a process called reverse transcription. Following transport into the cell nucleus, the proviral DNA is integrated in a host chromosome, permanently altering the genome of the infected cell and any progeny cells that may arise. The ability to permanently introduce a gene encoding a polypeptide or oligonucleotide into a cell such as a HUCPVC is the defining characteristic of retroviruses used for gene therapy. Retroviruses include lentiviruses, a family of viruses including human immunodeficiency virus (HIV) that includes several accessory proteins to facilitate viral infection and proviral integration. Additional examples of retroviruses include: avian leukosis-sarcoma, mammalian C-type, B-type viruses, D-type viruses, HTLV-BLV group, and spumavirus.

A retrovirus for gene therapy may be one that is modified to direct the insertion of the donor gene incorporated in the genome of the virus into a non-arbitrary position in the genome of the host, e.g., using a zinc finger nuclease or by including sequences, such as the beta-globin locus control region, to direct the site of integration to specific chromosomal sites. Retroviruses and lentiviruses have considerable utility for gene therapy applications. Current, "third-generation" lentiviral vectors feature total replication incompetence, broad tropism, and increased gene transfer capacity for mammalian cells. Lentiviruses pseudotyped with, e.g., vesicular stomatitis virus glycoprotein (VSV-G) or feline endogenous virus RD114 envelope glycoprotein can be used to transduce HUCPVCs. U.S. Pat. Nos. 5,919,458, 5,994, 136, and 7,198,950, hereby incorporated by reference, describe the production and use of lentiviruses to genetically modify target cells.

Besides adenoviral and retroviral vectors, other viral vectors and techniques are known in the art that can be used to transfer a donor gene encoding a desired polypeptide or oligonucleotide (e.g., a gene encoding a transcription factor or any other gene product) into a subject or cells. These viruses include, e.g., poxviruses (e.g., vaccinia virus and modified vaccinia virus Ankara (MVA); see, e.g., U.S. Pat. Nos. 4,603,112 and 5,762,938), herpesviruses, togaviruses (e.g., Venezuelan Equine Encephalitis virus; see, e.g., U.S. Pat. No. 5,643,576), picornaviruses (e.g., poliovirus; see, e.g., U.S. Pat. No. 5,639,649), and baculoviruses. Other viruses useful for delivering donor genes include papovavirus, hepadnavirus, and hepatitis virus, for example.

Naked DNA or oligonucleotides (e.g., DNA vectors such as plasmids) encoding transcription factors or any other gene products can also be used to genetically modify fibroblasts. This is the simplest method of non-viral transfection. Clinical trials carried out using intramuscular injection of a naked DNA plasmid have had some success; however expression has been low in comparison to other methods of transfection. Other efficient methods for delivery of naked DNA exist such as electroporation and the use of a "gene gun," which shoots DNA-coated gold particles into the cell using high pressure gas.

To improve the delivery of a DNA vector (e.g., a plasmid) into fibroblasts, the DNA can be protected from damage and its entry into the cell facilitated. Lipoplexes and polyplexes have the ability to protect transfer DNA from undesirable degradation during the transfection process. Plasmid DNA can be covered with lipids in an organized structure like a micelle or a liposome. When the organized structure is complexed with DNA it is called a lipoplex. There are three types of lipids, anionic (negatively-charged), neutral, or cationic (positively-charged). Lipoplexes that utilize cationic lipids have proven utility for gene transfer. Cationic lipids, due to their positive charge, naturally complex with the negatively charged DNA. Also as a result of their charge they interact with the cell membrane, endocytosis of the lipoplex occurs, and the DNA is released into the cytoplasm. The cationic lipids also protect against degradation of the DNA by the cell. Complexes of polymers with DNA are called polyplexes. Most polyplexes consist of cationic polymers and their production is regulated by ionic interactions. One large difference between the methods of action of polyplexes and lipoplexes is that polyplexes cannot release their DNA load into the cytoplasm, so to this end, co-transfection with endosome-lytic agents (to lyse the endosome that is made during endocytosis) such as inactivated adenovirus must occur. However, this is not always the case; polymers such as polyethylenimine have their own method of endosome disruption as does chitosan and trimethylchitosan.

In some embodiments gene editing is used to genetically modify fibroblasts. Broadly, gene editing approaches are based on precise, targeted changes to the genome of organisms. Gene editing may be used to alter the genome sequence (for example, by incorporation of point mutations, insertions, or deletions). Gene editing approaches can be used to 'knock-in' heterologous nucleic acid sequences into the genome at targeted locations. A variety of gene editing approaches are known in the art, including but not limited to clustered regularly interspaced short palindromic repeats (CRISPR)-Cas (e.g., Cas9) gene editing (see, e.g., U.S. Pat. Nos. 8,697,359 and 8,771,945), transcription activator-like effector based nuclease (TALEN) gene editing, zinc-finger nuclease (ZFN) gene editing, or meganuclease gene editing (see, e.g., U.S. Pat. No. 8,021,867).

V. Methods of Treatment

Embodiments of the disclosure include methods of treating an individual for a medical condition by providing to the individual fibroblasts and/or a product generated by or derived from said fibroblasts, including exosomes, apoptotic bodies, conditioned media, and so forth. In particular embodiments, the individual has an inflammatory disease, including an autoimmune disease, or is at risk for having an inflammatory disease, including an autoimmune disease as compared to the general population. The individual may be at risk for having one or more risk factors, such as a personal or family history, one or more genetic markers, and so forth. The compositions of the disclosure may be used for in vivo, in vitro, or ex vivo administration.

The therapy provided herein may comprise administration of a combination of therapeutic compositions, such as a first inflammatory disease therapy (e.g., fibroblasts and/or a product generated by or derived from said fibroblasts) and one or more additional inflammatory disease therapies. The therapies may be administered in any suitable manner known in the art. For example, the first and one or more additional inflammatory disease therapies may be administered sequentially (at different times) or concurrently (at the same time or approximately the same time; also "simultaneously" or "substantially simultaneously"). In some embodiments, the first and one or more additional inflammatory disease therapies may be administered in a separate composition. In some embodiments, the first and one or more additional inflammatory disease therapies may be in the same composition. The different therapies may be administered in one composition or in more than one composition, such as 2 compositions, 3 compositions, or 4 compositions. Various combinations of the agents may be employed.

A. Carriers

In some embodiments, pharmaceutical compositions of the present disclosure comprise an effective amount of one or more compositions comprising fibroblasts and/or a product generated by or derived from said fibroblasts dissolved or dispersed in a pharmaceutically acceptable carrier. The phrases "pharmaceutical" and "pharmacologically acceptable" and used interchangeably herein refer to molecular entities and compositions that do not produce an adverse, allergic or other untoward reaction when administered to a subject, such as, for example, a human, as appropriate, and do not interfere with the therapeutic methods of the disclosure. The preparation of a pharmaceutical composition that comprises fibroblasts and/or a product generated by or derived from said fibroblasts, or additional active ingredient(s), will be known to those of skill in the art in light of the present disclosure, as exemplified by Remington: The Science and Practice of Pharmacy, 21st Ed. Lippincott Williams and Wilkins, 2005, specifically incorporated by reference herein in its entirety. Moreover, for administration to a subject, it will be understood that preparations should meet sterility, pyrogenicity, general safety, and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, specifically incorporated by reference herein in its entirety). Except insofar as any conventional carrier is incompatible with the active ingredient, its use in the pharmaceutical compositions is contemplated. The compositions comprising fibroblasts and/or a product generated by or derived from said fibroblasts may comprise different types of carriers depending on whether it is to be administered in solid, liquid or aerosol form, and whether it needs to be sterile for such routes of administration, such as injection.

Further in accordance with the present disclosure, the composition of the present disclosure suitable for administration may be provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a composition contained therein, its use in practicing the methods of the present disclosure is appropriate. Examples of carriers or diluents include fats, oils, water, saline solutions, lipids, liposomes, resins, binders, fillers, alcohols, and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present disclosure, the composition is combined with the carrier in any convenient and practical manner, i.e., by solution, suspension, emulsification, admixture, encapsulation, absorption and the like. Such procedures are routine for those skilled in the art. The compositions comprising fibroblasts and/or a product generated by or derived from said fibroblasts may be lyophilized.

In a specific embodiment of the present disclosure, the composition is combined or mixed thoroughly with a semisolid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in the composition include buffers, amino acids such as glycine and lysine, carbohydrates such as dextrose, mannose, galactose, fructose, lactose, sucrose, maltose, sorbitol, mannitol, etc.

In further embodiments, the present disclosure may include the use of a pharmaceutical lipid vehicle compositions that incorporate compositions comprising fibroblasts and/or a product generated by or derived from said fibroblasts, one or more lipids, and an aqueous solvent. As used herein, the term "lipid" will be defined to include any of a broad range of substances that is characteristically insoluble in water and extractable with an organic solvent. This broad class of compounds is well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present disclosure.

One of ordinary skill in the art would be familiar with the range of techniques that can be employed for dispersing a composition in a lipid vehicle. For example, the composition(s) comprising fibroblasts and/or a product generated by or derived from said fibroblasts may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The composition(s) comprising fibroblasts and/or a product generated by or derived from said fibroblasts may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

A. Routes of Administration

The therapeutic agents of the disclosure may be administered by the same route of administration or by different routes of administration. The route of administration of the composition may be, for example, intravenously, intracerebrally, intracranially, intramuscularly, subcutaneously, topically, orally, mucosally, intradermally, transdermally, intraperitoneally, intraarterially, intraorbitally, by implantation, intravaginally, intrarectally, intrathecally, intraarticularly, intraventricularly, intrasynovially, or intranasally; by inhalation, injection, infusion, continuous infusion, localized perfusion bathing target cells directly, via a catheter, via a lavage; in creams or in lipid compositions (e.g., liposomes); by other method or any combination of the forgoing as would be known to one of ordinary skill in the art (see, for example, Remington's Pharmaceutical Sciences, 18th Ed. Mack Printing Company, 1990, specifically incorporated by reference herein in its entirety).

In some embodiments, the composition(s) comprising fibroblasts and/or a product generated by or derived from said fibroblasts is delivered systemically or locally. In some embodiments, the composition comprising fibroblasts and/or a product generated by or derived from said fibroblasts is delivered by peripheral injection, such as intravenous injection.

1. Parenteral Routes

Thus, in some embodiments, the composition(s) comprising fibroblasts and/or a product generated by or derived from said fibroblasts may be administered via a parenteral route. As used herein, the term "parenteral" includes routes that bypass the alimentary tract. Specifically, the pharmaceutical compositions disclosed herein may be administered for example, but not limited to retro-orbitally, intracerebrally, intracranially, intravenously, intradermally, intramuscularly, intraarterially, intrathecally, subcutaneous, or intraperitoneally U.S. Pat. Nos. 6,7537,514, 6,613,308, 5,466,468, 5,543, 158; 5,641,515; and 5,399,363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (see, e.g., U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in isotonic NaCl solution and injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions may be prepared by incorporating the active compounds in the required amount in the appropriate solvent with various of the other ingredients enumerated above, as required, followed by filtered sterilization, for example. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

2. Alimentary Routes

In particular embodiments of the present disclosure, the composition(s) comprising fibroblasts and/or a product generated by or derived from said fibroblasts is formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792,451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration, the composition(s) comprising fibroblasts and/or a product generated by or derived from said fibroblasts of the present disclosure may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively, the compositions may be fashioned into a tablet or solution form that may be placed under the tongue or otherwise dissolved in the mouth.

Additional formulations that are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10% (by weight), and preferably about 1% to about 2% (by weight).

3. Miscellaneous Routes

In other embodiments of the disclosure, the composition(s) comprising fibroblasts and/or a product generated by or derived from said fibroblasts may be formulated for administration via various miscellaneous routes, for example, topical (i.e., transdermal) administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-soluble based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and laurocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present disclosure may also comprise the use of a "patch". For example, the patch may supply one or more active substances at a predetermined rate and in a continuous manner over a fixed period of time.

In certain embodiments, the pharmaceutical composition(s) comprising fibroblasts and/or a product generated by or derived from said fibroblasts may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (see, e.g., Takenaga et al., 1998) and lysophosphatidyl-glycerol compounds (see, e.g., U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in, e.g., U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present disclosure for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

B. Dosing

The appropriate dosage amount of a composition(s) of the present disclosure administered to the subject can be determined by physical and physiological factors such as body weight, severity and course of condition, the type of disease being treated, the clinical condition of the individual, previous or concurrent therapeutic interventions, the individual's clinical history and response to the treatment, idiopathy of the subject, the route of administration, and the discretion of the attending physician. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% (by weight) of an active compound. In other embodiments, the active compound may comprise between about 2% to about 75% of the weight of the unit, or between about 25% to about 60%, for example, and any range derivable therein. Naturally, the amount of active compound(s) in each therapeutically useful composition may be prepared in such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

The treatments may include various "unit doses." Unit dose is defined as containing a predetermined-quantity of the therapeutic composition. The quantity to be administered, and the particular route and formulation, is within the skill of determination of those in the clinical arts. A unit dose need not be administered as a single injection but may comprise continuous infusion over a set period of time. In some embodiments, a unit dose comprises a single administrable dose.

The quantity to be administered, both according to number of treatments and unit dose, depends on the treatment effect desired. An effective dose is understood to refer to an amount necessary to achieve a particular effect. Furthermore, such doses can be administered at multiple times during a day, and/or on multiple days, weeks, or months.

In some embodiments, the dose of fibroblasts is 1000/kg body weight to 5 million/kg body weight. In certain aspects, it is 1000-5 million, 1000-4 million, 1000-3 million, 1000-2 million, 1000-1 million, 1000-500,000, 1000-250,000, 1000-100,000, 1000-10,000 cells/kg body weight.

Precise amounts of the therapeutic composition also depend on the judgment of the practitioner and are peculiar to each individual. Factors affecting dose include physical and clinical state of the patient, the route of administration, the intended goal of treatment (alleviation of symptoms versus cure) and the potency, stability and toxicity of the particular therapeutic substance or other therapies a subject may be undergoing.

VI. Kits of the Disclosure

Any of the cellular and/or non-cellular compositions described herein or similar thereto may be comprised in a kit. In a non-limiting example, one or more reagents for use in methods for treatment of inflammation may be comprised in a kit. Such reagents may include fibroblasts, derivatives thereof, media, enzymes, buffers, nucleotides, salts, primers, and so forth. The kit components are provided in suitable container means.

Some components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present disclosure also will typically include a means for containing the components in close confinement for commercial sale. Such containers may include injection or blow molded plastic containers into which the desired vials are retained.

When the components of the kit are provided in one and/or more liquid solutions, the liquid solution is an aqueous solution, with a sterile aqueous solution being particularly useful. In some cases, the container means may itself be a syringe, pipette, and/or other such like apparatus, or may be a substrate with multiple compartments for a desired reaction.

Some components of the kit may be provided as dried powder(s). When reagents and/or components are provided as a dry powder, the powder can be reconstituted by the addition of a suitable solvent. It is envisioned that the solvent may also be provided in another container means. The kits may also comprise a second container means for containing a sterile acceptable buffer and/or other diluent.

In specific embodiments, reagents and materials include primers for amplifying desired sequences, nucleotides, suitable buffers or buffer reagents, salt, and so forth, and in some cases the reagents include apparatus or reagents for isolation of a particular desired cell(s).

In particular embodiments, there are one or more apparatuses in the kit suitable for extracting one or more samples from an individual. The apparatus may be a syringe, fine needles, scalpel, and so forth.

EXAMPLES

The following examples are included to demonstrate certain non-limiting aspects of the invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention.

Example 1

Suppression of TNF-Alpha Production by LPS-Activated Monocytes by Proliferating Fibroblasts Monocytes were collected and plated at a concentration of 200,000 per ml and cultured together with fibroblasts (mitotically inactivated by 5 ug mitomycin C), proliferating fibroblasts, as well as the endotoxin Lipopolysaccharides (LPS) at the indicated concentrations. TNF-alpha was assessed by ELISA. See FIG. 1. Blue bars (far left) are control cultures, dark orange bars (second from left) is LPS treated alone, grey bars (second from right) are LPS together with mitomycin C inactivated fibroblasts, and light orange bars (far right) are LPS treated together with proliferating fibroblasts. TNF-alpha production was greatly reduced from LPS-activated monocytes in the presence of proliferating fibroblasts.

Example 2

Figure 2:
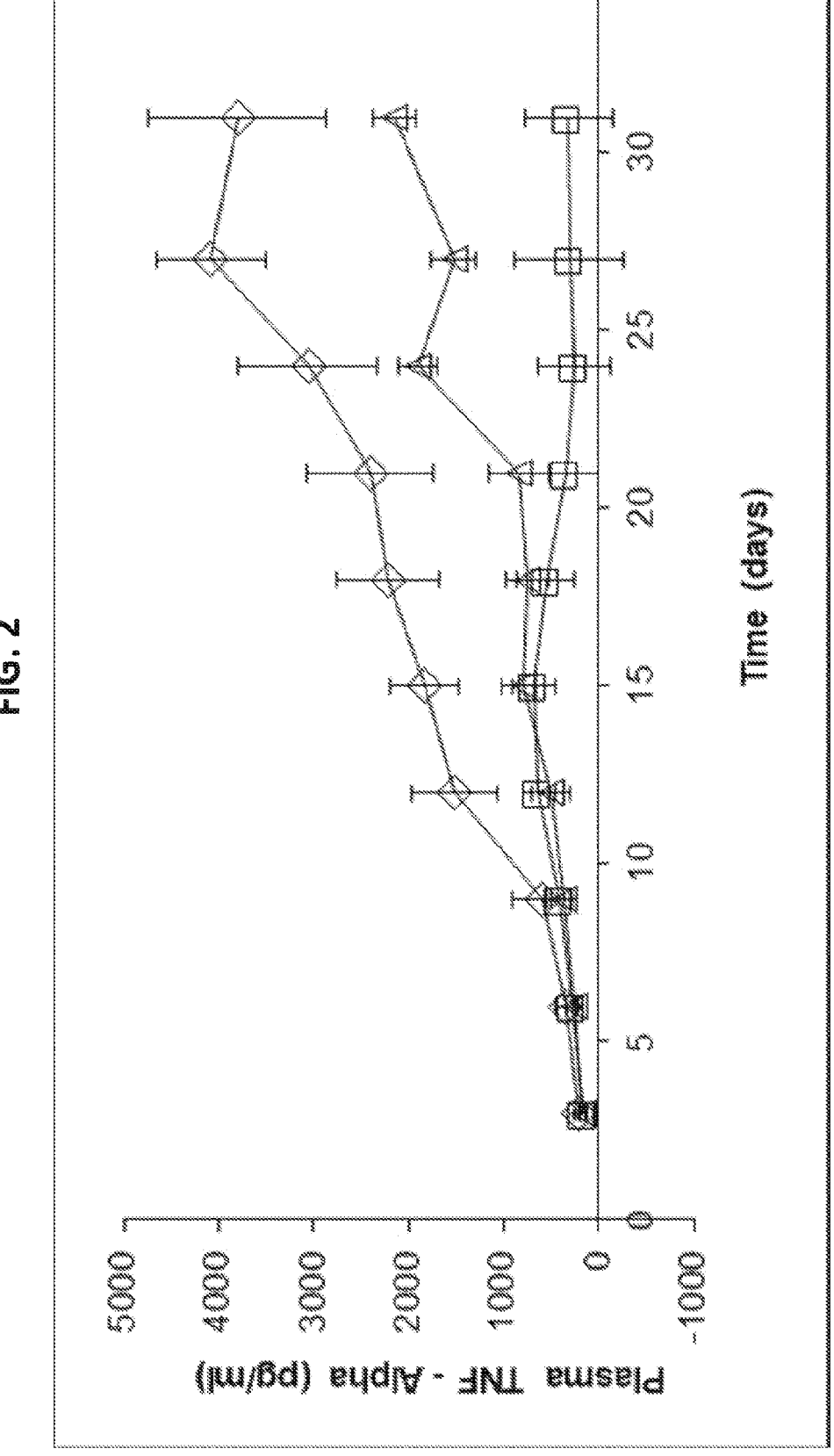
FIG. 2 shows in vivo suppression of TNF-alpha production in serum of mice injected with collagen as described in [31] using treatment with proliferating fibroblasts (squares) compared to treatment with mitotically inactivated fibroblasts (triangles) and saline only (diamonds).

In Vivo Suppression of TNF-Alpha Production in Serum of Collagen Induced Arthritis Inactivated fibroblasts (mitotically inactivated by 5 ug mitomycin C), proliferating fibroblasts, or controls were injected once every three weeks in collagen-induced arthritic mice after the second injection of collagen as described [31]. See FIG. 2. Diamonds were controls who received saline. Triangles represent mice that received 500,000 mitomycin C-inactivated fibroblasts, and squares are the mice that received 500,000 proliferating fibroblasts. Suppression of TNF-alpha was observed in the animals that received proliferating fibroblasts.

Example 3

Suppression of Monocyte TNF-Alpha Production by Fibroblast Exosomes

Figure 3:
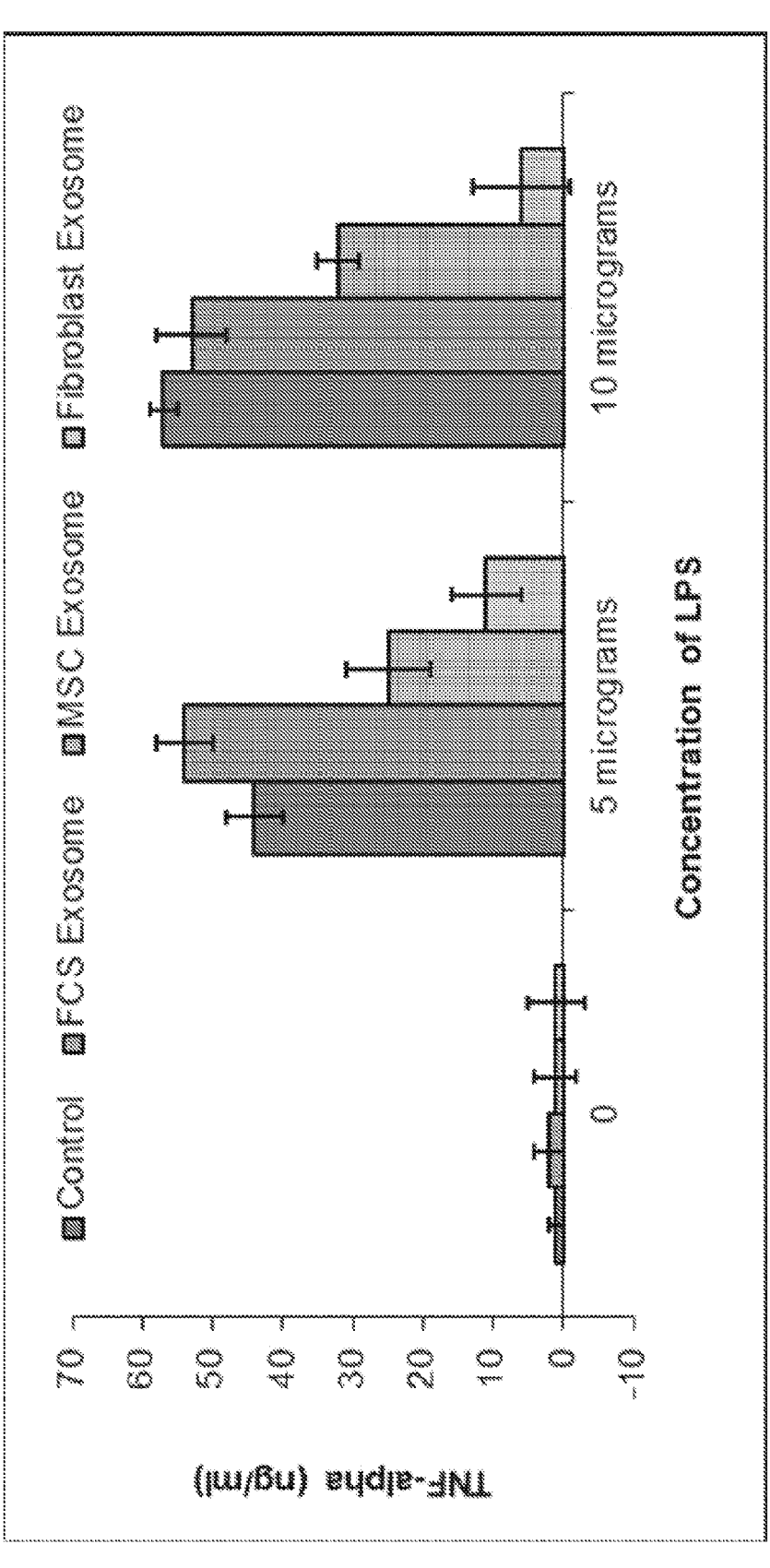
FIG. 3 shows in vitro suppression of TNF-alpha production by LPS activated monocytes using treatment with fibroblast derived exosomes compared to treatment with bone marrow mesenchymal stem cell (MSC) derived exosomes, fetal calf serum (FCS) derived exosomes, and control media alone. The order of bars on the figure from left to right are control media alone, FCS derived exosomes, MSC derived exosomes, and fibroblast derived exosomes.

Monocytes were collected and plated at a concentration of 200,000 per ml and cultured together with control media, fetal calf serum derived exosomes, bone marrow mesenchymal stem cell-derived exosomes, and fibroblast-derived exosomes, as well as endotoxin at the indicated concentrations. Cells and exosomes were incubated for 48 hours and TNF-alpha was assessed by ELISA (FIG. 3).

Exosomes were generated by concentration of fetal calf serum, bone marrow MSC conditioned media, or fibroblast conditioned media, by a first centrifugation of 30 minutes at 500 g to remove debris. The supernatant was subsequently centrifuged at 100,000 g for 2 hours to collect the exosome pellet. Exosomes were incubated at concentration of 100 nanograms per ml. Exosome concentration was assessed by total concentration of protein using the Bradford Assay. The order of bars on the figure from left to right are control, FCS exosome, MSC exosome, and fibroblast exosome. TNF-alpha production from monocytes was significantly reduced in the presence of fibroblast-derived exosomes.

US 12,576,112 B2

25

Example 4

Suppression of Monocyte TNF-Alpha Production
by CD73 Fibroblast Exosomes

Monocytes were collected and plated at a concentration of 200,000 per ml and cultured together with control media, fetal calf serum (FCS)-derived exosomes, bone marrow mesenchymal stem cell (MSC)-derived exosomes, and fibroblast-derived exosomes, as well as endotoxin at the indicated concentrations. Cells and exosomes were incubated for 48 hours and TNF-alpha was assessed by ELISA (see FIG. 4).

Figure 4:
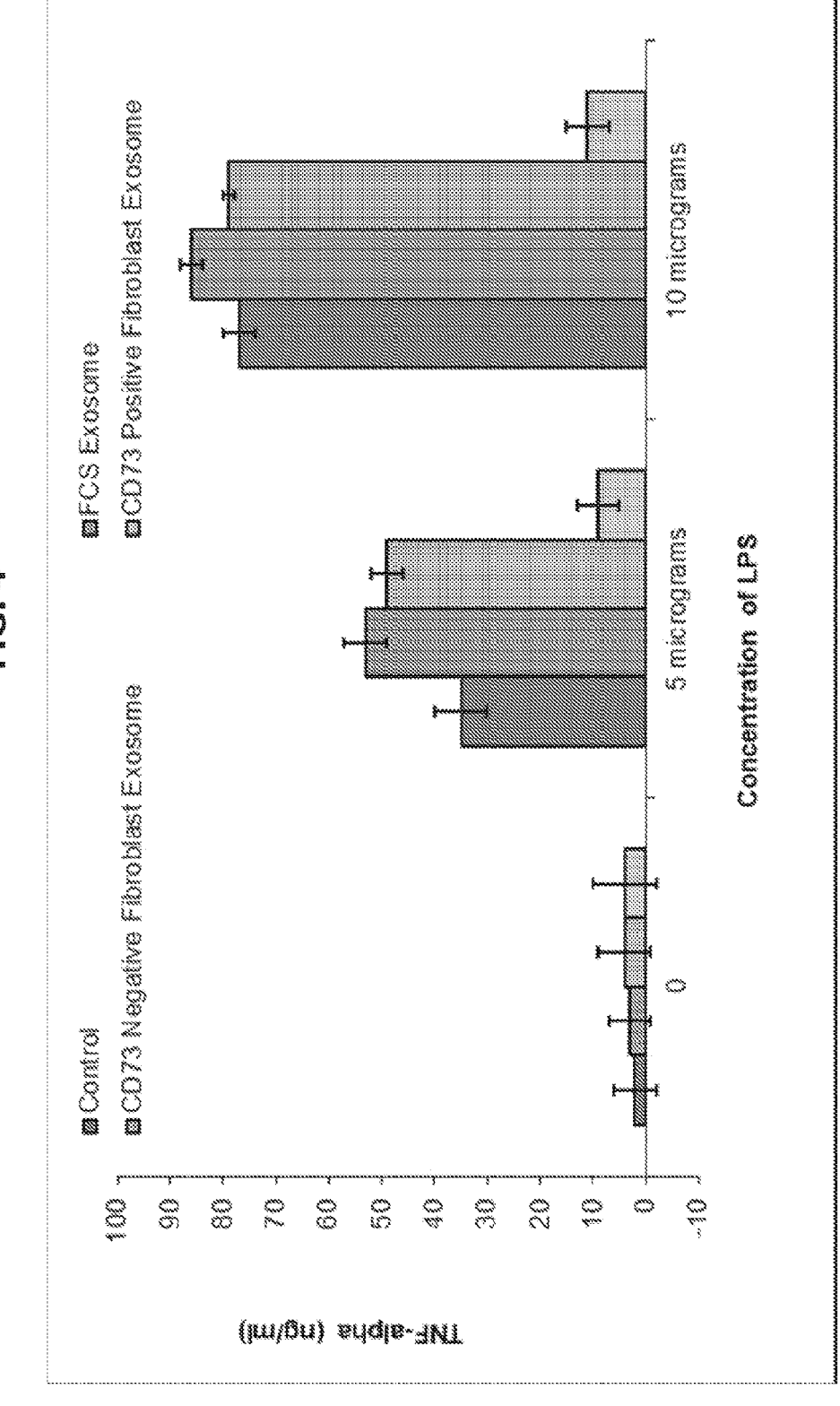
FIG. 4 shows in vitro suppression of TNF-alpha production by LPS activated monocytes using treatment with CD73-positive fibroblast exosomes as compared to CD73-negative fibroblast exosomes, fetal calf serum (FCS) derived exosomes, and control media alone. The order of bars on the figure from left to right are control media alone, FCS derived exosomes, CD-73-negative fibroblast exosomes, and CD-73 positive fibroblast exosomes.

Exosomes were generated by concentration of fetal calf serum and conditioned media from CD73-positive and CD73-negative exosomes, by a first centrifugation of 30 minutes at 500 g to remove debris. The supernatant was subsequently centrifuged at 100,000 g for 2 hours to collect the exosome pellet. CD73 positive and CD73 negative fibroblasts were isolated by use of Magnetic Activated Cell Sorting (MACS) according to the manufacturer's instructions. Exosomes were incubated at concentration of 100 nanograms per ml. Exosome concentration was assessed by total concentration of protein using the Bradford Assay (FIG. 4). The order of bars on the graph from left to right is control, FCS exosome, CD73-negative fibroblast exosomes, and CD73-positive fibroblast exosomes. As shown, a decrease in TNF-alpha production was observed with the CD73 negative fibroblast co-culture and the CD73 positive fibroblast co-culture, with CD73 positive fibroblast co-culture having the greatest suppression on TNF-alpha production.

Example 5

Figure 5:
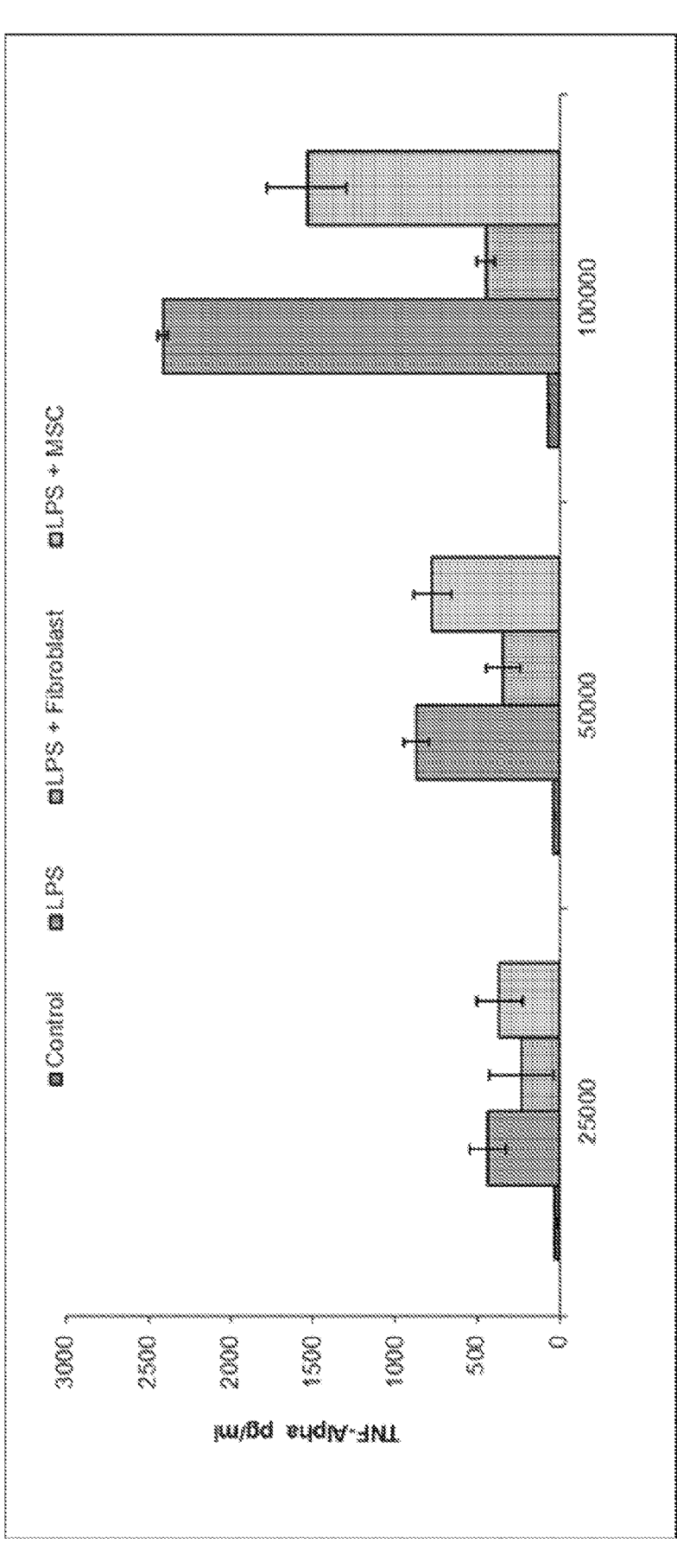
FIG. 5 shows in vitro suppression of TNF-alpha production by LPS-activated cortical astrocytes derived from inducible pluripotent stem cells using treatment with foreskin fibroblast exosomes as compared to MSCs, LPS only, and control media alone. The order of bars on the figure from left to right are control media alone, LPS only, MSCs, and fibroblasts.

Suppression of TNF-Alpha Production by
LPS-Activated Cortical Astrocytes by Foreskin
Fibroblasts Cortical astrocytes derived from inducible pluripotent stem cells were purchased from BrainXell and cultured at concentrations of 25,000, 50,000, or 100,000 cells per well in flat bottom 96-well plates. Cells were activated with LPS (50 ng/ml) for 48 hours in the presence of 25,000 fibroblasts (foreskin fibroblasts from ATCC) or 25,000 bone marrow mesenchymal stem cells (MSCs). Production of TNF-alpha was quantified by ELISA (FIG. 5). The order of bars on the graph from left to right is control media alone, LPS only, LPS and fibroblasts, and LPS and MSCs. As shown, a substantial decrease in TNF-alpha was observed with the fibroblast co-culture.

REFERENCES

All patents and publications mentioned in the specification are indicative of the level of those skilled in the art to which the invention pertains. All patents and publications are herein incorporated by reference in their entirety to the same extent as if each individual publication was specifically and individually indicated to be incorporated by reference.

1. O'Malley, W. E., B. Achinstein, and M. J. Shear, *Journal of the National Cancer Institute*, Vol. 29, 1962: *Action of bacterial polysaccharide on tumors. II. Damage of sarcoma 37 by serum of mice treated with Serratia marcescens polysaccharide, and induced tolerance*. Nutr Rev, 1988. 46(11): p. 389-91.
2. Carswell, E. A., et al., *An endotoxin-induced serum factor that causes necrosis of tumors*. Proc Natl Acad Sci USA, 1975. 72(9): p. 3666-70.
3. Pennica, D., et al., *Human tumour necrosis factor: precursor structure, expression and homology to lymphotoxin*. Nature, 1984. 312(5996): p. 724-9.
4. Wang, A. M., et al., *Molecular cloning of the complementary DNA for human tumor necrosis factor*. Science, 1985. 228(4696): p. 149-54.
5. Beutler, B., et al., *Identity of tumour necrosis factor and the macrophage-secreted factor cachectin*. Nature, 1985. 316(6028): p. 552-4.
6. Tracey, K. J., et al., *Cachectin/tumor necrosis factor induces cachexia, anemia, and inflammation*. J Exp Med, 1988. 167(3): p. 1211-27.
7. Tracey, K. J., et al., *Metabolic effects of cachectin/tumor necrosis factor are modified by site of production. Cachectin/tumor necrosis factor-secreting tumor in skeletal muscle induces chronic cachexia, while implantation in brain induces predominantly acute anorexia*. J Clin Invest, 1990. 86(6): p. 2014-24.
8. Black, R. A., et al., *A metalloproteinase disintegrin that releases tumour-necrosis factor-alpha from cells*. Nature, 1997. 385(6618): p. 729-33.
9. Ruddle, N. H. and B. H. Waksman, *Cytotoxicity mediated by soluble antigen and lymphocytes in delayed hypersensitivity. 3. Analysis of mechanism*. J Exp Med, 1968. 128(6): p. 1267-79.
10. Kolb, W. P. and G. A. Granger, *Lymphocyte in vitro cytotoxicity: characterization of human lymphotoxin*. Proc Natl Acad Sci USA, 1968. 61(4): p. 1250-5.
11. Spahn, T. W., et al., *Role of lymphotoxin in experimental models of infectious diseases: potential benefits and risks of a therapeutic inhibition of the lymphotoxin-beta receptor pathway*. Infect Immun, 2005. 73(11): p. 7077-88.
12. Aggarwal, B. B., S. C. Gupta, and J. H. Kim, *Historical perspectives on tumor necrosis factor and its superfamily: 25 years later, a golden journey*. Blood, 2012. 119(3): p. 651-65.
13. Cabal-Hierro, L. and P. S. Lazo, *Signal transduction by tumor necrosis factor receptors*. Cell Signal, 2012. 24(6): p. 1297-305.
14. Park, Y. H., M. S. Jeong, and S. B. Jang, *Structural insights of homotypic interaction domains in the ligand-receptor signal transduction of tumor necrosis factor (TNF)*. BMB Rep, 2016. 49(3): p. 159-66.
15. Ham, B., et al., *The diverse roles of the TNF axis in cancer progression and metastasis*. Trends Cancer Res, 2016. 11(1): p. 1-27.
16. Marchetti, L., et al., *Tumor necrosis factor (TNF)-mediated neuroprotection against glutamate-induced excitotoxicity is enhanced by N-methyl-D-aspartate receptor activation. Essential role of a TNF receptor 2-mediated phosphatidylinositol 3-kinase-dependent NF-kappa B pathway*. J Biol Chem, 2004. 279(31): p. 32869-81.
17. Brenner, D., H. Blaser, and T. W. Mak, *Regulation of tumour necrosis factor signalling: live or let die*. Nat Rev Immunol, 2015. 15(6): p. 362-74.
18. Cowburn, A. S., et al., *The survival effect of TNF-alpha in human neutrophils is mediated via NF-kappa B-dependent IL-8 release*. Eur J Immunol, 2004. 34(6): p. 1733-43.
19. Hamid, T., et al., *Divergent tumor necrosis factor receptor-related remodeling responses in heart failure: role of nuclear factor-kappaB and inflammatory activation*. Circulation, 2009. 119(10): p. 1386-97.

20. Hsu, H., J. Xiong, and D. V. Goeddel, *The TNF receptor 1-associated protein TRADD signals cell death and NF-kappa B activation*. Cell, 1995. 81(4): p. 495-504.

21. Huang, J., et al., *Structural basis of cell apoptosis and necrosis in TNFR signaling*. Apoptosis, 2015. 20(2): p. 210-5.

22. Rothe, M., et al., *TRAF2-mediated activation of NF-kappa B by TNF receptor 2 and CD40*. Science, 1995. 269(5229): p. 1424-7.

23. Grell, M., et al., *The transmembrane form of tumor necrosis factor is the prime activating ligand of the 80 kDa tumor necrosis factor receptor*. Cell, 1995. 83(5): p. 793-802.

24. Deng, J., et al., *TNFR-1 on tumor cells contributes to the sensitivity of fibrosarcoma to chemotherapy*. Protein Cell, 2013. 4(5): p. 393-401.

25. Huang, P., et al., *Endothelial expression of TNF receptor-1 generates a proapoptotic signal inhibited by integrin alpha6beta1 in glioblastoma*. Cancer Res, 2012. 72(6): p. 1428-37.

26. Chopra, M., et al., *Exogenous TNFR2 activation protects from acute GvHD via host T reg cell expansion*. J Exp Med, 2016. 213(9): p. 1881-900.

27. Okubo, Y., et al., *Treg activation defect in type 1 diabetes: correction with TNFR2 agonism*. Clin Transl Immunology, 2016. 5(1): p. e56.

28. Polz, J., et al., *Myeloid suppressor cells require membrane TNFR2 expression for suppressive activity*. Immun Inflamm Dis, 2014. 2(2): p. 121-30.

29. Cui, L. F., et al., *Overexpression of TNF-alpha and TNFRII in invasive micropapillary carcinoma of the breast: clinicopathological correlations*. Histopathology, 2008. 53(4): p. 381-8.

30. Yang, F., Z. Zhao, and N. Zhao, *Clinical implications of tumor necrosis factor receptor 2 in breast cancer*. Oncol Lett, 2017. 14(2): p. 2393-2398.

31. Zheng, X., et al., *Treatment of autoimmune arthritis using RNA interference-modulated dendritic cells*. J Immunol, 2010. 184(11): p. 6457-64.

The invention claimed is:

1. A method of suppressing production of TNF-alpha from a cell, comprising contacting cells capable of producing TNF-alpha with an effective amount of fibroblasts in a proliferated state and/or a conditioned medium generated by said fibroblasts, wherein the cells capable of producing TNF alpha are microglial cells and/or astrocyte cells.

2. The method of claim 1, wherein said cells capable of producing TNF-alpha are mammalian cells.

3. The method of claim 1, wherein said fibroblasts express one or more of Oct-4, Nanog, Sox-2, KLF4, c-Myc, Rex-1, GDF-3, LIP receptor, CD105, CD117, CD344, Stella, CD10, CD13, CD44, CD73, CD90, CD141, PDGFr-alpha, HLA-A, HLA-B, HLA-C, FoxD3, and Polycomb embryonic transcription factors and/or wherein the fibroblasts do not express one or more of MHC class I, MHC class II, CD44, CD45, CD13, CD49c, CD66b, CD73, CD105, CD90, CD31, CD34, CD117, CD141, and HLA-DR, DP,DQ.

4. The method of claim 1, wherein the fibroblasts are separated from cells selected from the group consisting of granulocytes, T-cells, B-cells, NK-cell, red blood cells, cells expressing stem cell surface markers, cells expressing MHC proteins, or any combination thereof, prior to said contacting step.

5. The method of claim 1, wherein the population of said fibroblasts are in a proliferative state and are enriched prior to said contacting step, the enriching step further comprising the steps of:

contacting said fibroblasts with a detectable compound that enters the fibroblasts, wherein the compound is selectively detectable in proliferating and non-proliferating fibroblasts; and enriching the population of fibroblasts for proliferating fibroblasts.

6. The method of claim 1, wherein said fibroblasts are transfected with Oct-4, Nanog, Sox-2, and/or KLF prior to said contacting step.

7. The method of claim 6, wherein said fibroblasts further comprise enhanced regenerative activity compared to a control.

8. The method of claim 1, wherein said fibroblasts are fused with cells having a pluripotent ability prior to said contacting step;

wherein said fibroblast cells expressing CD 105 and/or CD 117 are transfected with permeant NANOG gene;

wherein fibroblasts are cultured under conditions that form tissue aggregate bodies prior to said contacting step;

wherein fibroblasts are cultured under conditions that support fibroblast proliferation prior to said contacting step; and/or wherein said fibroblasts are activated with one or more agents that resembles inflammation prior to said contacting step.

9. The method of claim 8, wherein said fibroblasts further comprise enhanced regenerative activity compared to a control.

10. The method of claim 8, wherein said fibroblasts further comprise rhodamine 123 efflux activity as compared to a control.

11. The method of claim 8, wherein said fibroblasts further comprise enhanced expression of GDF-11 as compared to a control.

12. The method of claim 1, wherein the contacting step occurs in vivo, and wherein said effective amount of said fibroblasts and/or a conditioned medium generated by said fibroblasts is provided to an individual in need thereof.

13. The method of claim 12, wherein the individual has or is at risk for an inflammatory disease.

14. The method of claim 13, wherein suppression of TNF-alpha comprises suppression of the effects of TNF-alpha on cells in the individual.

15. The method of claim 14, wherein said suppression of effects of TNF-alpha comprises suppression of vascular leakage in the individual;

suppression of NF-kappa B activation in the individual;

suppression of tissue factor expression in the individual; or suppression of upregulation of complement activators in the individual.

16. The method of claim 1, wherein said conditioned medium generated by said fibroblast comprises exosomes and/or apoptotic bodies generated by said fibroblasts.

17. The method of claim 16, wherein said exosomes express phosphatidylserine on their membrane and/or is CD73 positive.

\* \* \* \* \*